United States Patent [19]

Donohue

[11] Patent Number: 5,020,524
[45] Date of Patent: Jun. 4, 1991

[54] MODULAR DIGITAL TRACTION SYSTEM

[76] Inventor: Patrick T. Donohue, 1822 NE. 143rd, Portland, Oreg. 97230

[21] Appl. No.: 389,698

[22] Filed: Aug. 3, 1989

[51] Int. Cl.⁵ .......................... A61F 5/04; A61F 5/10
[52] U.S. Cl. .................................. 128/84 C; 128/77; 128/87 A; 128/84 R
[58] Field of Search ............... 128/75, 77, 84 R, 84 C, 128/87 A, 878, 879, 26, 28

[56] References Cited

U.S. PATENT DOCUMENTS

| | | |
|---|---|---|
| 1,305,749 | 6/1919 | Shirley . |
| 3,533,405 | 10/1970 | Collins . |
| 3,595,225 | 7/1971 | Beeman . |
| 4,220,334 | 9/1980 | Kanamoto . |
| 4,297,992 | 11/1981 | Larue . |
| 4,441,489 | 4/1984 | Evans et al. ................. 128/87 A |
| 4,665,905 | 5/1987 | Brown ........................ 128/84 R |
| 4,675,914 | 6/1987 | Mitchell . |
| 4,719,906 | 1/1988 | DeProspero ................. 128/77 |
| 4,830,360 | 5/1989 | Carr, Jr. . |
| 4,944,290 | 7/1990 | Hepburn ..................... 128/77 |

OTHER PUBLICATIONS

Catalog: "Orthopaedics 1989", Fred Sammons, Inc., Burr Ridge, Illinois-pp. B12-14, B18, B21 and B22.

Primary Examiner—Richard J. Apley
Assistant Examiner—Lynne A. Reichard
Attorney, Agent, or Firm—Bruce J. Ffitch

[57] ABSTRACT

A therapeutic traction system comprises two principal modules—a bandage-like traction band module for applying to a finger or other digit and a spring module. A minmum working combination consists of two traction band modules with a spring module connected between them so as to bias them apart. Traction band modules may vary in the number and orientation of connecting elements to which a spring module may be connected. Spring modules are elongated coil springs which, in use, are usually deflected into a bow form and, optionally, also torsionally deflected, to create the desired biasing force.

37 Claims, 2 Drawing Sheets

MODULAR DIGITAL TRACTION SYSTEM

BACKGROUND OF THE INVENTION

The invention concerns orthotic devices for applying forces or pressures at the joints of the human body and more particularly for applying traction and other manipulative forces at the digits of the extremities, especially the hands. Devices called "lively" splints may be included in this group.

Certain non-malignant conditions, such as arthritis and the like, cause unnatural pull on the tendons and muscles of the hand and result in painful joints, deformity and sometimes partial or total loss of use of the hand. Pain may be experienced because a phalanx is pulled out of normal position in relation to another phalanx or the metacarpal bone, causing the respective joint to move out of normal position. Or the digital bones or phalanxes of a digit may become displaced with respect to each other as a result of unnatural pull on or displacement of the tendons and muscles resulting in a misalignment or distortion of the digit.

Devices which apply an axial force (traction) across a joint, or opposing lateral forces on opposite sides of a joint, tend to return the joint to a more normal configuration and relieve pain. A number of devices of this general type are known, but while they may function satisfactorily they suffer from variety of limitations. Most of them are single purpose, providing only one function, and individual units may require custom fitting to particular digits or to the extremity as a whole and may not be readily adaptable to another application. Some devices severely limit the mobility of individual digits or of the whole extremity. The net cost of using such devices may be relatively high, both because of the high cost of manufacture of a relatively complicated design and the duplication required because of lack of adaptability of the design. For example, the devices disclosed in U.S. Pat Nos. 3,533,405, Collins, 3,595,225 Beeman and 4,220,334 Kanamoto all have a single purpose or mode of application. Certainly no device is known which provides two or more functions from a group of functions comprising: applying traction; applying opposing lateral forces at a joint; and applying separating forces between two digits. No simple device is known for applying traction at an individual interphalangeal joint of a digit.

SUMMARY OF THE INVENTION

Accordingly it is an object of the invention to provide a simple low cost orthotic arrangement for influencing the joints of the body and particularly interphalangeal and other joints of the extremities. Preferably, the arrangement has more than one mode of use, both in terms of the nature of the forces applied and the positions on the extremity at which they are applied.

It is an associated object to provide a system which, even though it may provide forces other than traction may for convenience be called a modular traction system, and may comprise a small number of individual components (modules) a selection from which may be connected together and mounted on the extremity.

The system may comprise two basic modules—a traction band for substantially encircling a digit and gripping it so that the band is not displaced when an external therapeutic force is applied to the band and hence into the digit, and an elongated resilient biasing element. Preferably each traction band carries at least one connecting element accessible externally of the band when the band is in position on a digit. Opposite ends of the resilient biasing element are each connectable to a connecting element of a traction band. A minimum functioning unit or combination of the modular traction system may consist of two traction bands mounted on an extremity with, for example, one band one each side of an interphalangeal joint or one band on each of adjacent digits, with a single resilient biasing element connected between them in such a way as to bias them apart. An advantage of the system if that the biasing element may "bridge" the portion of the extremity being treated (an interphalangeal joint for example) so that there is no direct contact with the treated portion and it may remain exposed.

Another object of the invention is to provide a traction band module for a digital traction system which is readily and reliably secured to a digit and which incorporates a connecting element for connection to an external biasing element so that an external force may be applied to the digit. Preferably the traction band is adaptable to a range of digit sizes and its structure facilitates low cost manufacture so that it may be considered a disposable or throw-away module of the traction system.

Preferred embodiments of the invention may include a traction band in the form of a flexible bandage for wrapping a digit and having a soft inner lining of foam rubber or the like with an adhesive coating to secure the band and prevent it from slipping on the digit. A flexible but stiffer outer layer of the band may carry the connecting element either formed as an integral part of the outer layer or cover or at least rigidly attached to it. The resilient biasing element may be an elongated spring having opposite ends, each end being releasably connectible with a connecting element of a traction band. Preferably each connecting element is formed so that it has a directional axis and so that when a spring is connected the end of the spring extends in a fixed predetermined direction, with respect to the traction band. Advantageously, a modular traction system according to the invention may include interchangeable biasing element modules (springs) of various strengths, to suit particular applications.

Traction bands may carry more than one connecting element so that three or more traction bands may be used in combination (connected by two or more biasing elements). Orientation of the directional axes of connecting elements on any one traction band may be mixed, so that in an application of three or more traction bands to an extremity more than one spring configuration and force mode may be used. Preferably the spring is an elongated coil spring wound with initial tension so that it stores potential energy efficiently when subjected to either bending or torsional deflection. The force applied at a connecting element of a traction band may thus be a simple translational force or a combination of translational force and torsion.

A traction system according to the invention is thus versatile, simple and potentially low in cost. Its simplicity and low cost particularly qualify it for self application and management by the patient with a minimum of physician supervision, as required.

DESCRIPTION OF THE PREFERRED EMBODIMENTS

Figure 1:
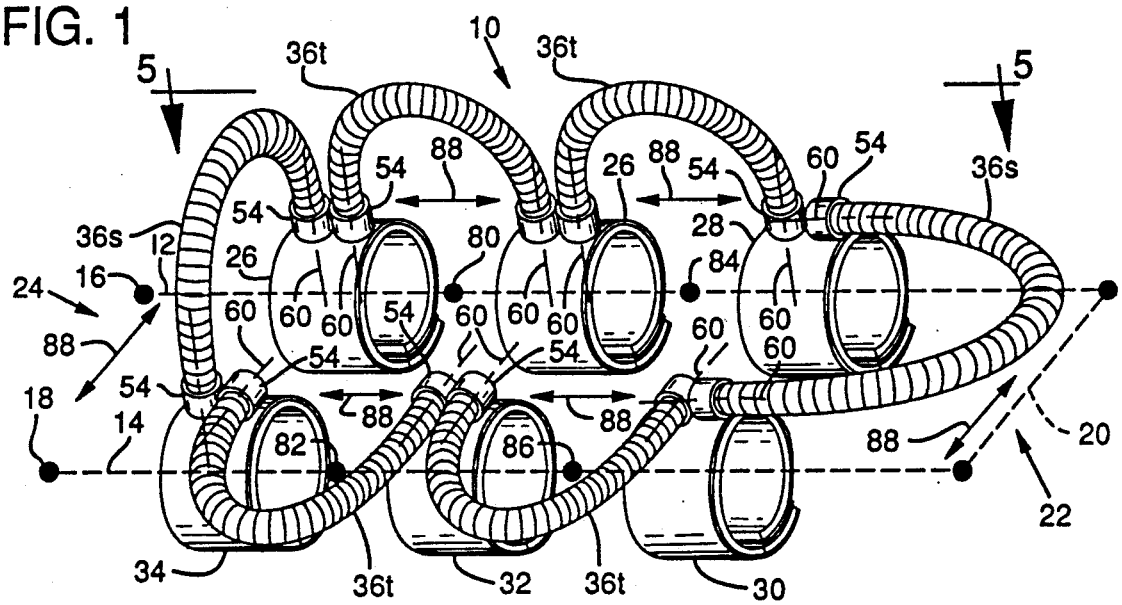
FIG. 1 is a semi-schematic perspective view of modules of a traction system according to the invention assembled into a possible arrangement for two adjacent fingers and including five different embodiments of a traction band.

The invention is embodied in the exemplary traction system arrangement 10 shown in FIG. 1. The system is usable to develop manipulative forces at the joints other than pure traction but, for convenience, it will be referred to as a traction system. The system concepts may be embodied in devices adapted for use at the joints of fingers and toes and at other joints such as knees, and elbows, but, again for convenience, the following description and discussion will refer only to the digits of the hand.

The arrangement 10 of FIG. 1 is shown semi-schematically. Although such an arrangement of traction system modules may feasibly be applied to a hand, the main purpose of the figure is to show, in a single grouping, several embodiments of traction band module according to the invention and how they may be used together.

The system 10 is mounted on adjacent first and second digits 12 and 14, respectively, indicated only by their longitudinal axes. Each finger has a tip, 16, 18 respectively. Finger crotch 20 extends between the fingers. The traction system arrangement 10 thus has a palm end 22 and a finger tip end 24.

A traction system according to the invention is made up of traction band and spring modules. In FIG. 1, first through fifth embodiments of traction band are shown and designated by numerals 26-34 respectively. A single embodiment of spring module, spring 36 is shown.

Figure 2:
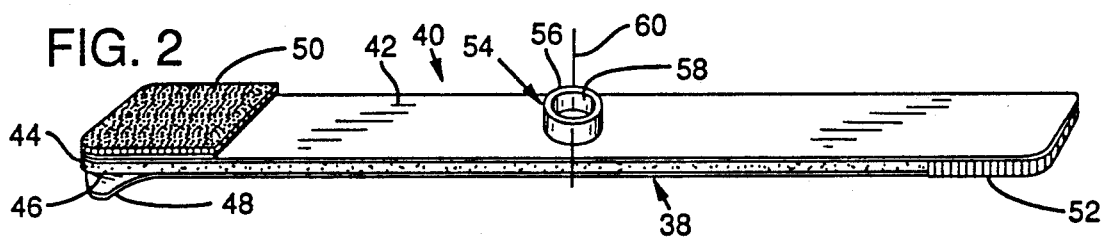
FIG. 2 is a perspective view of a sixth embodiment of the traction band before mounting on a digit and characterized in having a single connecting element and a Velcro (TM) type fastener for supplementing the securing of the ends of the band and giving it limited reusability.

Common elements of all traction bands are a band portion for substantially wrapping and securing the traction band to a digit, and a connecting element for connecting to a second module such as spring 36. A sixth embodiment of traction band, traction band 38, is shown in FIG. 2, and the common features of embodiments 1-6 will be described with reference to FIG. 2 which shows a traction band in its free, as received, condition before application to a digit. The layered construction of the band portion 40, from outside to inside, consists of: thin plastic sheet material forming an outer cover 42; a somewhat resilient lining 44 which may be of foam rubber and preferably has an adhesive coated inner face 46; and a peel-off backing strip 48 to protect the adhesive face 46 until the traction band is mounted. Patches of Velcro (TM) type hook and loop fastener material 50, 52 respectively are mounted on the opposite ends and on opposite sides of the cover strip 42.

Each traction band 26 through 34 and 38 carries at least one connecting element 54 and the traction bands of this group are distinguished only in the number and orientation of connecting elements 54. The connecting element 54 has a simple cylindrical form with a wall 56 defining an aperture or receptacle 58, and a central longitudinal axis 60 which may be regarded as a directional axis as explained below. The connecting elements 54 may be of a suitable plastic material and, either attached to the cover strip 42 by a suitable method such as cementing or hot fusion, or may be formed integrally with the cover strip 42 by a suitable method such as injection molding.

Figure 3:
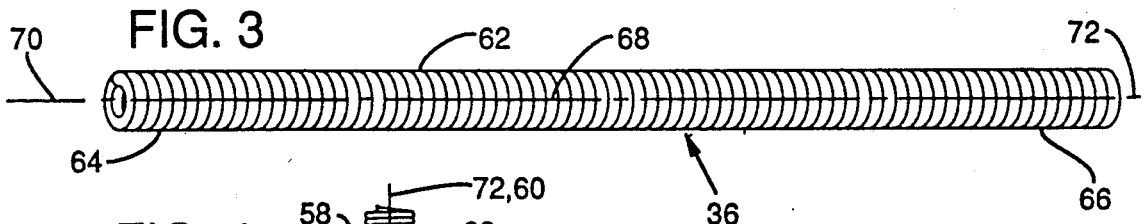
FIG. 3 is a perspective view of a spring module as used in the arrangement of FIG. 1, shown in its free condition.

Spring 36 of the spring module shown in its free state in FIG. 3, is preferably a coil spring of steel wire closely wound, with initial tension between the coils 62, and preferably with squared ends 64, 66 respectively. First and second end portions of the longitudinal axis 68 of the spring are designated 70, 72 respectively. Other forms of elongated spring or spring material having suitable beam deflection (and preferably torsional deflection) characteristics may be used. For example solid spring steel wire may be used, possibly partially bowed in its free state (not shown).

Figure 7:
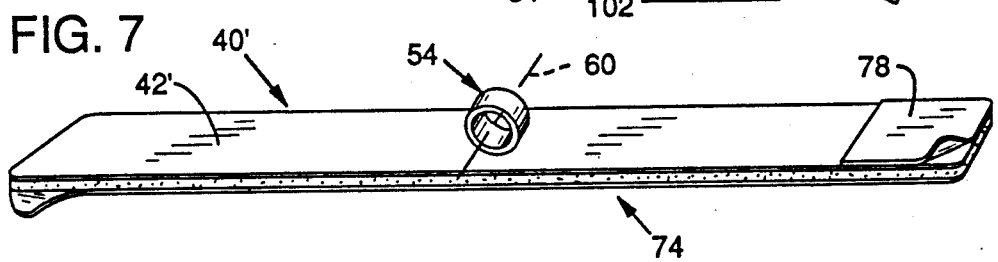
FIG. 7 is a perspective view of an uninstalled traction band basically conforming to the seventh embodiment shown in FIG. 6, but including an alternative means of supplementing the securing of the end of the band when mounted on a digit.
Figure 8:
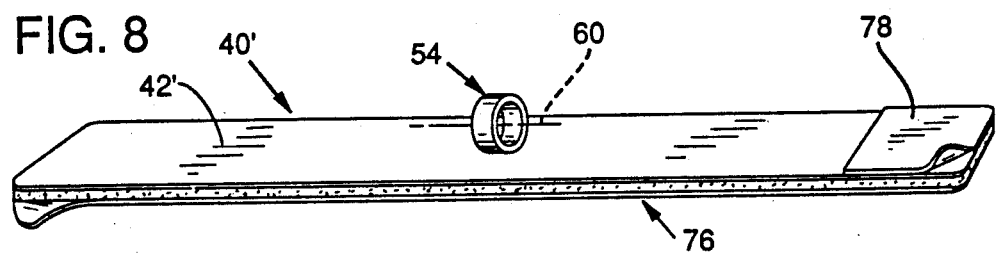
FIG. 8 is a view similar to FIG. 7 of an eighth embodiment of traction band.

FIGS. 7 and 8 show respectively seventh and eighth embodiments 74, 76 of traction band. They are characterized principally by the orientation of their connecting elements 54. These elements are disposed so that, in use, their directional axes 60 would extend parallel to the axis of the digit and transverse or tangential to the digit respectively. The band portions 40' of these two embodiments may have the same layered construction as that described with reference to FIG. 2 but the Velcro (TM) type end fastenings (50, 52) have been dispensed with. As an alternative, an end of the band cover 42' has been coated with an adhesive (not shown), protected until the traction band is used by a conventional peel-off backing piece 78. Suitable traction band construction may take many additional forms including, for example, a form similar to that of FIGS. 7 and 8 but without the extra adhesive backing (covered by 78). Preferably, such constructions have a potentially low manufacturing cost so that they are affordably disposable (e.g. FIGS. 7 and 8). Or, with a minimum of cost increase, such as the addition of a Velcro (TM) type fastener (FIG. 2), they may be give at least limited reusability.

Figure 9:
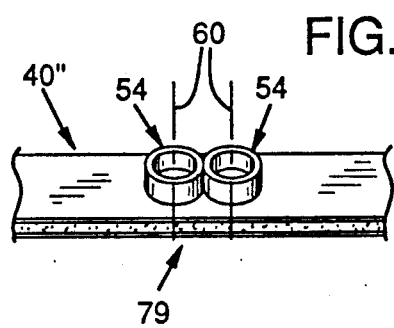
FIG. 9 is a partial view, similar to FIGS. 2 or 7, of a ninth embodiment of traction band.

FIG. 9 shows a ninth embodiment 79 of traction band. Two connecting elements 54 are disposed on band portion 40" so that, in use, their directional axes 60 are circumferentially spaced. In an exemplary application of this embodiment three or more bands 79 may be placed on adjacent digits and connected by springs 36, to spread the digits. An advantage of this traction band configuration is that all connecting elements 54 would be in convenient transverse alignment (not shown in the drawings). Other variations of traction band with circumferentially spaced connecting elements are potentially useful (for example, an arrangement with mutually perpendicular axes) but are not shown in the drawings.

Figure 4:
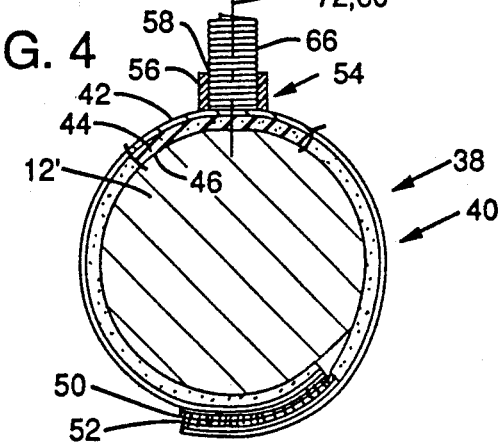
FIG. 4 is a cross sectional view taken approximately on line 4—4 of FIG. 5 showing a traction band in end view, partially sectioned to show the engagement of a spring module in the connecting element of a traction band.

An important aspect of a traction system according to the invention is the connection of the spring module (36) to the traction band (38). FIG. 4 illustrates the seating of a spring module end 66 in the receptacle 58 of a connecting element 54. Preferably the spring end 66 is held firmly but releasably by the connecting element 54 so that their respective longitudinal axes 72, 60 approximately coincide (or at least are approximately parallel). Preferably the grip of the spring by the connecting element is sufficient to allow some torsional deflection to ba applied to the spring before assembly and then held in assembly. The tightly wound coil spring of this exemplary embodiment is particularly advantageous in this application in that, although the fit of the spring in the connecting element after assembly may be adequately tight, the well-known, slight diameter reducing yielding of the spring under torsion (in one direction) allows it to be readily twisted into and out of assembly when turned in the appropriate direction. Also, the fit of the spring end 66 in connecting element 54 may be such that the spring may be "snapped" into and out of engagement. A particular "male/female" connection relationship is illustrated here. Clearly the relationship could be reversed with the connecting element (54) becoming a pin, entering the end 66 of the spring. Preferably, in any alternative connection arrangement, the connecting element carried by the traction band should determine the alignment of the spring at the point of connection. Clearly, the modular traction system may include interchangeable springs (biasing elements) 36 of various strengths to suit particular applications. To achieve this, wire size or initial tension, for example, may be changed.

FIG. 4 also illustrates the traction band 38 of FIG. 2 firmly gripping the finger 12'. The resilient liner 44 both increases comfort for the patient and helps to stabilize the traction band on the finger. The mating of the Velcro (TM) elements 50, 52 enhances the security of the band on the finger and also permits limited reusability of the band. Preferably the traction band cover portion 42 is sufficiently stiff so that in assembly it defines a relatively regular cylindrical form and provides a substantially non-yielding base for the connecting element 54, so that any force applied to the connecting element is transferred effectively and efficiently to the finger 12". In keeping with the invention, other forms of traction band construction may be used. But it is important that a band provide support for a connecting element, such as element 54 which is stable and secure so that an external therapeutic force may be transferred comfortably and efficiently to the digit on which it is mounted. In particular any band securing method must hold the band against axial or rotational movement on the digit. For hygienic and other reasons a preferred construction of traction band is one which makes the band affordably disposable, similar for example to the construction shown in FIGS. 2 and 4.

Figure 5:
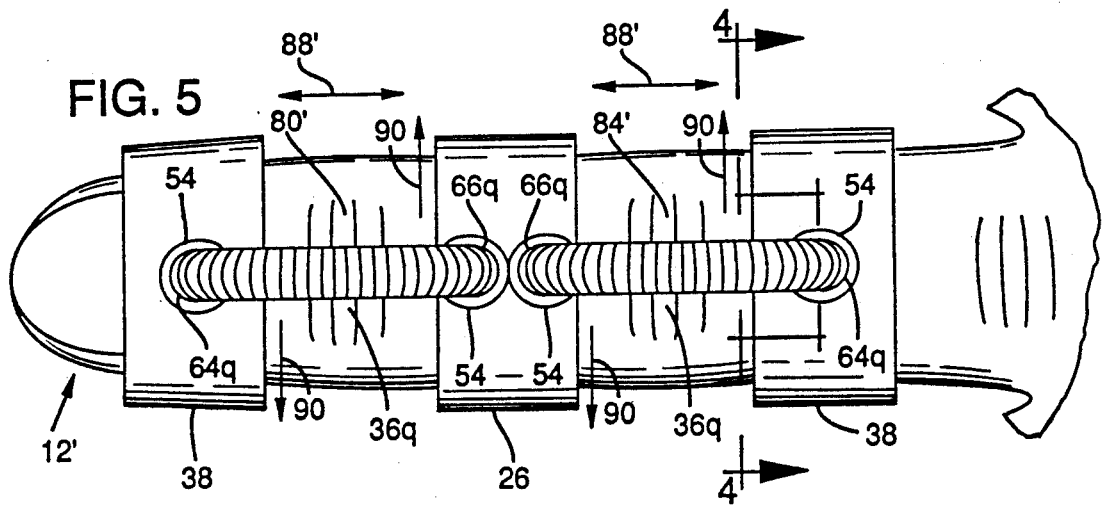
FIG. 5 is an overhead view similar to a view on line 5—5 of FIG. 1 showing the traction system applied to the two interphalangeal joints of a single digit and indicating the additional force effect at an interphalangeal joint of torsionally deflecting the spring module before completing the mounting of the module on the digit.
Figure 6:
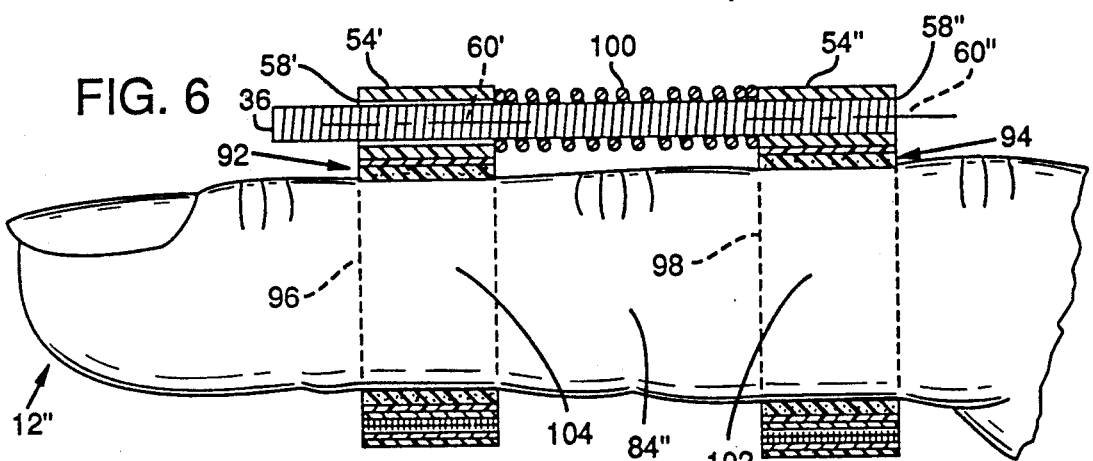
FIG. 6 is a side elevation of a finger with a traction system mounted and shown in longitudinal cross section. Two variations of a seventh embodiment of traction band are shown.

An indication of the versatility of a traction system according to the invention is give, collectively, the arrangements shown in FIGS. 1, 5 and 6.

The "demonstration" arrangement 10 of FIG. 1 produces both traction and a separation force on the digits. The traction bands 26–34, all of the same general construction as that shown in FIG. 2, are mounted on the respective distal, middle and proximal phalanges of the fingers 12, 14 so that there is a traction band on each side of the distal and proximal interphalangeal joints 80, 82 and 84, 86 respectively.

The five embodiments of traction band 26–34 included in the arrangement 10 of FIG. 1 are differentiated only in the orientation of their connecting elements 54. This orientation is usefully described with reference to the axis of the digit on which the traction band is mounted. Thus, traction bands 26, 28 and 34 all include connecting elements 54 whose directional axes are perpendicular to (and coplanar with) the longitudinal axes of the fingers on which they are mounted. Traction bands 28–34 all include connecting elements oriented in a plane parallel to but no intercepting the longitudinal axis of the fingers. The latter include connecting elements 54, with directional axes 60 parallel to the finger axis (traction bands 28 and 30) and others with directional axes 60 perpendicular to the longitudinal axis of the fingers (traction bands 30, 32, 34).

FIG. 1 illustrates four modes of application of the traction system. These four modes are exemplified by the traction band pairs (with associated spring modules) consisting of: two traction bands 26; traction bands 28 and 30; traction bands 32 and 34; and traction bands 26 and 34. At each pair a spring module 36 has been deflected into a bow and firmly connected to the respective elements 54. It is the nature of the spring 36 to attempt to straighten itself so that each pair of traction bands is subjected to a separating force, biasing them apart. The general direction of the separating forces is indicated by arrows 88. Thus, the interphalangeal joints 80, 84 and 82, 86 of the fingers 12 and 14 respectively are subjected to traction. On finger 12 the traction producing springs 36t are dorsally and vertically (radially) oriented so that a secondary effect of the springs is to tend to extend the finger (that is to straighten a finger which has been bent or flexed downwards). On finger 14 the traction producing springs 36t are also mounted dorsally, but extend horizontally (tangentially, in the general plane of the hand). In this orientation there are only minor secondary force effects of the springs. For example, flexing of the finger would encounter minor resistance or restoring force from the resultant torsional deflection of the springs.

Two orientations of digit separation force producing springs 36s also shown in FIG. 1. The "vertical" orientation is preferred at the finger tip end 24 of the arrangement because it leaves the patient more freedom to flex and extend the neighboring fingers 12 and 14, relative to one another. The "horizontal" orientation of the spring 36s at the palm end 22 of the hand may be preferred in that location. The spring lies neatly close to the back of the hand and is less of an encumbrance.

"Vertical" (radial) and "horizontal" (tangential) orientations of spring modules (36) have been discussed, referring to FIG. 1. But note that in FIG. 1 (and in FIGS. 5 and 6) all traction bands are mounted with their connecting elements (54) disposed dorsally. The traction system of the invention may also be used with other dispositions of the connecting element, including, but not limited to, palmar ("inside" the hand) and on the lateral sides of the digits. In some of these dispositions at least, radial or tangential spring orientations may have their respective advantages. It is a particular advantage of a system according to the invention that the biasing element (spring 36) always "bridges" the portion of the extremity being treated (an interphalangeal joint for example) so that there is no direct contact of the biasing element with the treated portion and it may remain exposed. And in all arrangements of the modules of the system there is only limited encumbrance of the hand. The traction bands (26 etc.) are only relatively narrow bandages. Bowed springs (36) do extend away from the digits with some potential for obstruction but choice of traction band embodiment (for preferred connecting element 54 orientation) and orientation of traction band on the digit may minimize any obstruction problem in a particular application.

In the traction system arrangement of FIG. 5, distal and proximal interphalangeal joints 80', 84' of finger 12' are being subjected to traction (in a manner similar to that of finger 12 in FIG. 1), employing one traction band 26 with twin connecting elements 54 and two traction bands 38 each with a single connecting element 54. The bowing deflection of the springs 36q in their connected state establishes an axially separating traction force indicated by the arrows 88' in the normal way. However, in this case, before the springs 36q were connected to the respective traction bands 26, 38 they were both twisted (torsionally deflected through a selectively variable angle). Thus a selectively variable secondary force, a torque, is produced at each connecting element 54 of the traction bands. One manifestation or application of the secondary torque effect is indicated in FIG. 5. It is assumed that the torsional deflection of both springs 36q was established in the following manner. Spring first ends 64a were each firmly inserted into the connecting elements 54 of traction bands 38. Then before connecting their opposite ends 66q into the connecting elements 54 of traction band 26, the springs 36q were "twisted" by rotationally deflecting the ends 66q in a clockwise direction as viewed from the ends 66q. One result of such "pre-loading" of the spring is to produce lateral opposing forces (arrows 90) on the opposite sides of each of the interphalangeal joints 80'84'. The application of such opposing lateral forces may assist in correcting misalignment brought about by arthritis or other conditions affecting normal movement of the digits, and in relieving associated pain.

FIG. 6 illustrates a second traction system mode for applying traction—in this case to the proximal interphalangeal joint 84" of finger 12". The traction bands 92, 94 mounted on the finger on opposite sides of the joint are of the seventh embodiment type shown in FIG. 7, characterized in that their connecting elements 54', 54" are, when in use, aligned with their directional axes 60' 60" parallel to the axis of the finger on which they are mounted. The construction of their respective band portions 96, 98 may be similar to the construction of the band portions of the traction bands shown in FIG. 2 or FIG. 7 and need not be described here. The connecting elements 54', 54" may, as shown in FIG. 6, be longer than the connecting elements 54 shown elsewhere, principally to give the particular support and guidance of the spring 36 appropriate for this traction applying mode. The receptacle 58" of connecting element 54" is sized to hold one end of the spring 36 firmly. The bore or receptacle 58' of the second connecting element 54' is sized to provide a sliding clearance for the other end of the spring. This traction arrangement introduces a third module to the system, compression spring 100 which, in use, is slipped over spring 36 and compressed and contained between the connecting elements 54', 54" and, because of the sliding fit of spring 36 in connecting element receptacle 58', is free to exert a separating or traction force on the respective traction bands 92, 94 and hence on the finger joint 84".

The "finger straightening" or finger extending effect of the linear spring 36 as applied in the arrangement of FIG. 6 when spring 100 is absent will be apparent. If the finger 12" is flexed downwards in a vertical plane (the plane of the paper as viewed in FIG. 6), spring 36 will be bowed and the normal self-straightening character of the spring will resist flexing of the finger and tend to re-extend it.

The arrangement of FIG. 6 also has a useful finger straightening capability in the horizontal plane. For example, arthritis, or some other condition, may have results in horizontal misalignment (not shown in the drawings) between the proximal and middle phalanges 102, 104 of the finger 12". Mounting of the traction system (traction bands 92, 94 and spring 36, in FIG. 6) on the finger will thus result in a deflection of the spring 36 from its normally straight condition, so that the spring will have a straightening effect on the finger.

A limited number of combinations of the elements of the invention, variations of structure, and modes of application have been described above to indicate the versatility of the system. Other useful variations will be apparent to a person of ordinary skill in the art and such variations are intended to fall within the scope of the claims which follow.

I claim:

1. A traction band for mounting on a digit of an extremity and facilitating the application of traction and other manipulative forces to the digit, the band being characterized in that it is engageable with the digit so as to substantially encircle it and so grip the digit that the band is displaced neither axially nor rotationally when the band is subjected to an externally applied manipulative force, and in that the application of the band to the digit establishes a generally cylindrical external surface of the band, the cylindrical surface having a longitudinal axis coinciding approximately with the longitudinal axis of the digit and in that the cylindrical surface carries at least one connecting element for connecting with an end of an elongated force exerting member and in that the connecting element has a directional axis extending generally perpendicular to the longitudinal axis of the cylindrical surface and is shaped to hold the end of the force exerting member so that the longitudinal axis of said end is parallel to the directional axis of the connecting element.

2. The traction band of claim 1 wherein the directional axis of the connecting element is coplanar with the longitudinal axis of the cylindrical surface.

3. The traction band of claim 1 wherein the directional axis of the connecting element does not intersect the cylindrical surface.

4. The traction band of claim 1 further characterized in that the band comprises an elongated flexible strip, said strip having an inner contact face which in use engages the digit and wherein the contact face is treated so as to inhibit slipping of the traction band with respect to the digit.

5. The traction band of claim 4 further characterized in that the opposite ends of the band overlap when applied to the digit and said opposite ends carry mating Velcro type fastening means.

6. The traction band of claim 1 wherein, when in use, the force exerting member is releasable from the connecting element.

7. The traction band of claim 1 wherein the connecting element comprises a hollow receptacle.

8. A traction system for use in applying traction and other manipulative forces to the digits of an extremity, each digit having a longitudinal axis, comprising:
   a first traction band for engaging and substantially encircling a first digit portion and being secured to that digit portion so as to be held against axial and rotational displacement relative to the digit portion;
   a second traction band for engaging and substantially encircling a second digit portion and being secured to that digit portion so as to be held against axial and rotational displacement relative to the digit portion; and
   elongated resilient biasing means connected between the first and second traction bands for biasing them apart in a direction generally parallel to the longitudinal axes of the respective digits.

9. The traction system of claim 8 wherein, in use, the traction bands are applied to the same digit and the biasing means includes a helical compression spring extending generally parallel to the axis of the digit.

10. A traction system for applying a traction force to a joint of a body member, the member having a longitudinal axis, comprising:
   first and second traction bands each gripping and substantially encircling the member and disposed respectively on first and second sides of the joint; and
   a spring for releasably connecting the first and second traction bands and biasing them apart in a direction generally parallel to the longitudinal axis of the member.

11. The traction system of claim 10 wherein each traction band includes a connector for releasably connecting with the spring, each connector having a directional axis and the directional axes being perpendicular to the longitudinal axis of the member, and wherein the spring is elongated and has a longitudinal axis and wherein, in assembly, the directional axis of each connector is parallel to an end portion of the longitudinal axis of the spring.

12. The method of applying traction to a joint of a digit of a human extremity, the digit having a longitudinal axis, comprising the steps of:
   securing a first traction band to the digit on one side of the joint;
   securing a second traction band to the digit on the other side of the joint; and
   connecting an elongated spring between the traction bands so that the spring exerts a separating force between the bands in a direction generally parallel to the longitudinal axis of the digit.

13. The method of claim 12 including the step of torsionally deflecting the spring so as to store torsional energy in the spring so that in operation, opposing lateral forces are generated at the joint of the digit.

14. A modular digital traction system for applying traction and other manipulation forces to the digits of a human extremity, each digit having a longitudinal axis and the system comprising:
   first and second elongated traction bands each for wrapping and being secured to a digit, said wrapping generating a generally cylindrical external surface of the band, each band having at least one connecting element accessible externally of the band when secured to a digit and each connecting element having a directional axis; and
   an elongated spring having opposite ends, each end having a longitudinal axis and each end being connectable with said at least one connecting element of a traction band, said connecting elements and spring opposite ends being formed so that when connected the longitudinal axes of the spring ends extend approximately parallel to the respective directional axis of the connecting element to which they are connected, and the connection of the spring to the traction bands causing a deflection of the spring so that, when connected, the traction bands are biased apart, and wherein, in use, the respective directional axes are parallel to each other and the spring, connected between them, defines a generally semi-circular form.

15. The traction system of claim 14 wherein, in use, the directional axis of each connecting element is perpendicular to the longitudinal axis of the digit on which it is mounted.

16. The traction system of claim 15 wherein the respective directional axes are coplanar with the longitudinal axis of the digit on which they are mounted.

17. The traction system of claim 15 wherein the respective directional axes of the connecting elements do not intersect the external cylindrical surfaces of their respective bands.

18. The traction system of claim 14 wherein, in use, the first and second bands are applied to the same digit.

19. The traction system of claim 18 and including a third traction band a second spring connected between the second and third traction bands.

20. The traction system of claim 19 wherein the second traction band includes two connecting elements.

21. The traction system of claim 14 wherein the respective first and second traction bands are applied to adjacent digits.

22. The traction system of claim 14 wherein the spring is a coil spring wound with initial tension so that it may store energy both by bending and by torsional deflection.

23. The traction system of claim 14 wherein, in use, the respective ends of the spring are fixed with respect to the connecting elements so that a torque may be applied to the traction band by the spring.

24. A traction system for applying traction and other manipulative forces to the digits of an extremity, each digit having a longitudinal axis, and the system comprising:
   first and second traction bands each for securing to a digit, each traction band having a connecting element having a directional axis, the connecting elements and the respective traction bands being disposed so that, in use, the directional axes are approximately parallel to the longitudinal axes of their respective digits; and
   an elongated resilient element having opposite ends, each end having a longitudinal axis and each end engaging a connecting element of a traction band so that the respective longitudinal axes of the ends of the resilient element are parallel to the directional axes of the connecting elements which they engage, and wherein the traction bands are mounted on the same digit and aligned so that the directional axes of the connecting elements are approximately coaxial, and the resilient element extends axially between the connecting elements and slidably engages at least one of the connecting elements.

25. The traction system of claim 24 wherein the resilient element means includes a compression spring contained between the connecting elements for biasing the elements axially apart.

26. A traction band for mounting on a digit of an extremity and facilitating the application of traction and other manipulative forces to the digit, the band being characterized in that it is engageable with the digit so as to substantially encircle it and so grip the digit that the band is displaced neither axially nor rotationally when the band is subjected to an externally applied manipulative force, and in that the application of the band to the digit establishes a generally cylindrical external surface of the band, the cylindrical surface having a longitudinal axis coinciding approximately with the longitudinal axis the digit and in that the cylindrical surface carries at least two connecting elements, each for connecting with an end of an elongated force exerting member and in that each connecting element has a directional axis and is shaped to hold the end of the force exerting member so that the longitudinal axis of said end is parallel to the directional axis of the connecting element.

27. The traction band of claim 26 wherein the directional axes of the connecting elements are spaced apart in a direction parallel to the longitudinal axis of the cylindrical surface.

28. The traction band of claim 26 wherein the directional axes of the connecting elements are circumferentially spaced with respect to the cylindrical surface.

29. The traction band of claim 27 wherein the directional axes of the connecting elements are parallel.

30. The traction band of claim 29 wherein the directional axes of the connecting elements are coplanar with the longitudinal axis of the cylindrical surface.

31. The traction band of claim 24 wherein the directional axes of the connecting elements do not intersect the cylindrical surface.

32. The traction band of claim 26 wherein the directional axes of the connecting elements are mutually perpendicular.

33. A traction system for use in applying traction and other manipulative forces to the digits of an extremity comprising:
a first traction band for engaging and substantially encircling a first digit portion and being secured to that digit portion so as to be held against axial and rotational displacement relative to the digit portion;
a second traction band for engaging and substantially encircling a second digit portion and being secured to that digit portion so as to be held against axial and rotational displacement relative to the digit portion; and
elongated resilient biasing means connected between the first and second traction bands for biasing them apart, the biasing means comprising an elongated spring having a length greater than the spacing between the traction bands so that, in use, the spring forms a bow extending between the traction bands.

34. The traction system of claim 33 wherein the first and second traction bands are applied to the same digit and are separated by at least one joint of that digit.

35. A traction system for use in applying traction and other manipulative forces to a digit of an extremity, the digit having at least two phalanges and an interphalangeal joint and a longitudinal axis, comprising:
a first traction band for engaging a first digit portion and being secured to that digit portion so as to be held against axial displacement relative to the digit portion;
a second traction band for engaging a second digit portion and being secured to that digit portion so as to be held against axial displacement relative to the digit portion; and
elongated resilient biasing means having opposite ends and connected between the first and second traction bands for biasing them apart in a direction generally parallel to the longitudinal axis of the digit,
wherein, in use, the biasing means is disposed and configured so as to arch generally dorsally with respect to the digit, spanning the interphlangeal joint and spaced from the joint so that the digit may be flexed without the biasing means coming into contact with the joint.

36. The traction system of claim 35 wherein each traction band includes a connecting point and the biasing means is connected to each band at its respective connecting point and, in use, the bands are arranged so that each connecting point is disposed generally dorsally of the digit.

37. The traction system of claim 35 wherein, in use, each traction band is also secured to its respective digit portion so as to be held against rotational displacement relative to the digit portion and each opposite end of the biasing means is connected to a band and is fixed in relation to the band to which it is connected and wherein relative torsional deflection of the respective opposite ends stores torsional energy in the biasing means so that a torque may be applied to each traction band by the biasing means and opposing lateral forces generated at the interphalangeal joint.

* * * * *